United States Patent [19]

Laforest

[11] 4,220,794
[45] Sep. 2, 1980

[54] SYNTHETIC INTERMEDIATES FOR THE PREPARATION OF DIAROMATIC O-(AMINO-ALKYL)OXIMES

[75] Inventor: Jacqueline Laforest, Vincennes, France

[73] Assignee: Albert Rolland S.A., Paris, France

[21] Appl. No.: 39,433

[22] Filed: May 15, 1979

[30] Foreign Application Priority Data

Jun. 8, 1978 [FR]  France ................................ 78 17159

[51] Int. Cl.$^2$ .................. C07D 333/22; C07D 307/20; A61K 31/34
[52] U.S. Cl. ................................ 549/77; 260/347.3; 424/275; 424/285; A61K/31/38
[58] Field of Search .................... 260/332.3 R, 347.3; 549/77

[56] References Cited

U.S. PATENT DOCUMENTS 4,116,974  9/1978  Farge et al. .................... 260/332.3 R Primary Examiner—A. Siegel Attorney, Agent, or Firm—Young & Thompson

[57] ABSTRACT

The present invention relates to compounds having the formula:

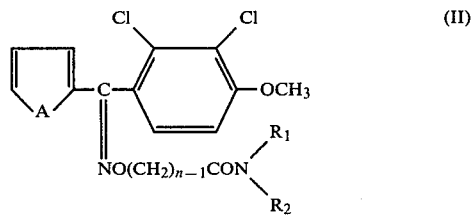

in which n is an integer from 1 to 4, A is selected from the group consisting of oxygen and sulfur and $R_1$ and $R_2$ are independently selected from the group consisting of hydrogen and $C_{1-4}$ alkyl.

These compounds are useful for the preparation of corresponding amino derivatives.

1 Claim, No Drawings

SYNTHETIC INTERMEDIATES FOR THE PREPARATION OF DIAROMATIC O-(AMINO-ALKYL)OXIMES

DESCRIPTION

This invention relates to the synthesis of therapeutically useful diaromatic O-(amino-alkyl)oximes which are therapeutically useful in view of their cardiotropic activity.

This invention relates more particularly to the synthesis of known compounds having the general formula:

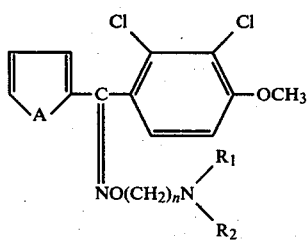

in which n is an integer from 1 to 4, A represents an oxygen or sulfur atom and $R_1$ and $R_2$ represent independently a hydrogen atom or a $C_{1-4}$ alkyl group. Such compounds and their utility are disclosed for example in U.S. Pat. No. 4,029,808.

The object of this invention is to provide a new route for the synthesis of compounds of the formula (I).

Therefore, this invention relates to new synthetic intermediates for the ready production of compounds of the formula (I).

The new synthetic intermediates are compounds having the formula:

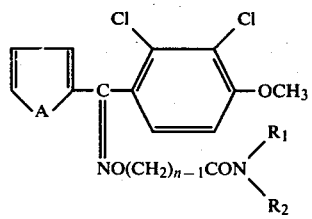

in which n, A, $R_1$ and $R_2$ have the above-defined meanings.

According to the present invention, the compounds of the formula (I) are obtained by reduction of compounds of the formula (II).

Said reduction may be effected with hydrogen, in the presence of catalysts, or preferably by action of hydrides.

Useful hybrides are, for example, lithium aluminum hydride, typically as a solution in an ether; diboran, as a solution in tetrahydrofuran; or an alkali metal borohydride in acid or basic medium.

The intermediate compounds of the formula (II) are advantageously prepared by reacting an oxime of the formula (III)

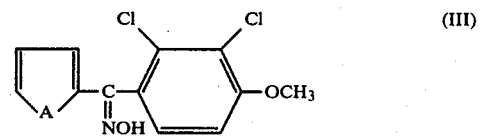

in which A has the above-defined meaning, with a chlorinated derivative having the formula:

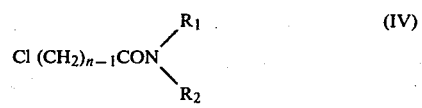

in which n, $R_1$ and $R_2$ have the above-defined meanings, in the presence, as hydrochloric acid binding agent, of a sufficiently weak base to prevent the substantial formation of a 1,2-benzisoxazole side-derivative having the formula:

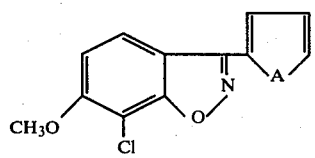

Useful weak bases include alkali metal carbonates or alkali earth metal carbonates, or amines such as methylamine and pyridine.

The reaction is preferably effected within dimethylformamide, in the presence of an alkali metal carbonate, at room temperature.

The following non-limiting Examples illustrate the present invention. It will be obvious to those skilled in the art that certain modifications may be brought to the operating conditions.

EXAMPLE 1

2-Thienyl-(2,3-dichloro-4-methoxy-phenyl)-O-(diethylaminoethyl)ketone oxime

A. 2-Thienyl-(2,3-dichloro-4-methoxy-phenyl)-O-(N-diethylcarbamoylmethyl-ketone oxime 2-Thienyl-(2,3-dichloro-4-methoxy-phenyl)ketone oxime (21.1 g) and N,N-diethyl chloroacetamide (21 g) are dissolved in N,N-dimethylformamide (160 ml), potassium carbonate (11 g) is added thereto and the mixture is left aside 24 hours at room temperature. The solid is filtered off, part of the solvent is removed under reduced pressure, the solution is poured over 200 ml water and the end product is extracted with an immiscible solvent such as ethyl ether or chloroform. Evaporation of the solvent gives 28 g solid material, a mixture of both oxime isomers.

The pure amide (M.p.=118° C.) is obtained by recrystallization from 95% aqueous ethanol.

B. Reduction

To a suspension of lithium aluminum hydride (0.47 g) in tetrahydrofuran (50 ml) is added a solution of the previously obtained amide (10 g) in tetrahydrofuran (30 ml), and the resulting material is refluxed for several hours. The excess hydride is decomposed, after which the material is hydrolyzed over ice. The aqueous phase is made alkaline by addition of potassium hydroxide and the organic products are extracted with ethyl ether.

The resulting amine is purified, taking into account its water-solubility in acidic medium.

These usual treatments give 7 g amine which is converted to the hydrochloride in ethyl ether by action of hydrochloric acid. The hydrochloric melts at 158° C.

EXAMPLE 2

2-Furyl-(2,3-dichloro-4-methoxy-phenyl)-O-(diethylaminoethyl)ketone oxime

A. (2,3-Dichloro-4-methoxy-phenyl)2-furyl-ketone oxime (22.88 g), N,N-diethylchloroacetamide (23.9 g) and potassium carbonate (13.8 g) in N,N-dimethylformamide (150 ml) are stirred for 24 hours. The solid is filtered off and the solvent and volatiles are distilled under reduced pressure. The residual oil may be purified by partition chromatography (silica column) using ethyl ether as eluent: it is a hygroscopic mixture of both oxime isomers, $n_D^{20} = 1.566$.

B. Reduction

To a suspension of lithium aluminum hydride (1.5 g) in ethyl ether (50 ml) is added a solution of the previously obtained amide (19.8 g) in ethyl ether (100 ml) and the mixture is refluxed for several hours. After decomposition of the excess hydride, the product is poured over ice and made alkaline by addition of potassium hydroxide, after which the organic products are extracted with a water-immiscible solvent. The final amine is separated from the decomposition products, while taking into account the water solubility of its methane sulfonic acid salt: the oil (14 g) obtained after evaporation of the solvent under reduced pressure is poured over water (100 ml) containing about 5 g methane sulfonic acid, and the insolubles are extracted with ethyl ether. The aqueous phase is then made alkaline and the desired amine is extracted with a solvent. After evaporation of the latter, 10.1 g pure amine, a mixture of both the oxime isomers, are isolated and are converted to the hydrochloride according to methods known per se. The hydrochloride melts at 150° C.

EXAMPLE 3

2-Thienyl-(2,3-dichloro-4-methoxy-phenyl)-O-(aminoethyl)ketone oxime.

A. 2-Thienyl-(2,3-dichloro-4-methoxy-phenyl)ketone oxime (11.8 g), chloroacetamide (5 g) and potassium carbonate (10 g) in N,N-dimethylformamide (80 ml) are stirred for 24 hours. The solid is removed by filtration and the solvent is evaporated under reduced pressure, to give 12 g solid containing some starting oxime. It may be purified by column chromatography (silica) using ether as eluent, followed by ether-methanol, or by recrystallization from 95% aqueous ethanol, to give 5.6 g of a product which melts at 158° C. and contains 25% of one of the oxime isomers.

B. Reduction

The reduction may be effected with the unrecrystallized previously obtained amide.

The crude amide (6.6 g) and sodium borohydride (3.45 g) are dissolved in dioxan (100 ml) and 5.49 g acetic acid dissolved in 20 ml dioxan are then added dropwise thereto, while maintaining the mixture at about 10° C. After several hours at room temperature, the mixture is refluxed for 3 hours, concentrated, poured over water and extracted with ether. The final amine is purified by dissolution in aqueous acidic medium, after which the solution is washed with an immiscible solvent and the aqueous phase is extracted after alkalinization, to give 4.5 g amine as an oil which is converted to the semi-oxalate by action of oxalic acid in ethanol. This is a mixture of both oxime isomers which melts at about 140° C.

EXAMPLE 4

2-Furyl-(2,3-dichloro-4-methoxy-phenyl)-O-(diethylaminoethyl)ketone oxime.

A molar solution of diboran in tetrahydrofuran (30 ml) is slowly poured into a solution of 2-furyl-(2,3-dichloro-4-methoxy-phenyl)-O-(N-diethylcarbamoylmethyl) ketone oxime (3.99 g) in anhydrous tetrahydrofuran (30 ml) maintained at 0° C. After stirring for several hours, the mixture is poured over water, made acidic by addition of hydrochloric acid and, after several hours, the medium is made alkaline and is then extracted with ethyl ether, to give 2.5 g amine, a mixture of both oxime isomers which may be separated by fractional crystallization of the amine hydrochloride from water. The hydrochloride melts at 150° C.

Having now described our invention what We claim as new and desire to secure by Letters Patent is:

1. A compound having the formula:

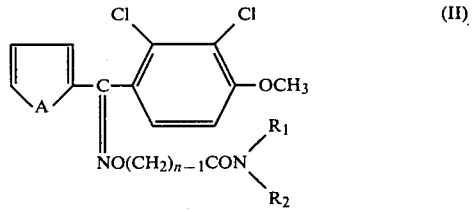

in which n is an integer from 1 to 4, A is selected from the group consisting of oxygen and sulfur and $R_1$ and $R_2$ are independently selected from the group consisting of hydrogen and $C_{1-4}$ alkyl.

* * * * *